US00PP17979P3

(12) United States Plant Patent
Drewlow et al.

(10) Patent No.: US PP17,979 P3
(45) Date of Patent: Sep. 4, 2007

(54) POINSETTIA PLANT NAMED 'GALA WHITE'

(50) Latin Name: *Euphorbia pulcherrima*
Varietal Denomination: Gala White

(75) Inventors: Lyndon W. Drewlow, Lompoc, CA (US); Gary Joe Wilfret, Sarasota, FL (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/300,838

(22) Filed: Dec. 15, 2005

(65) Prior Publication Data

US 2006/0156447 P1 Jul. 13, 2006

Related U.S. Application Data

(60) Provisional application No. 60/636,763, filed on Dec. 15, 2004.

(51) Int. Cl.
*A01H 5/00* (2006.01)

(52) U.S. Cl. ..... Plt./304

(58) Field of Classification Search ..... Plt./304, Plt./303

See application file for complete search history.

(56) References Cited

PUBLICATIONS

Internet website retrieval: NC State University—"Poinsettia Open House—2003 Commercial Floriculture" Oct. 2004—(9 pages total).*

* cited by examiner

*Primary Examiner*—Anne Marie Grunberg
*Assistant Examiner*—S. B. McCormick-Ewoldt
(74) *Attorney, Agent, or Firm*—The Webb Law Firm

(57) ABSTRACT

A new and distinct cultivar of Poinsettia plant named 'Gala White', characterized by its long-lasting white colored flower bracts and dark green foliage.

1 Drawing Sheet

Botanical classification: *Euphorbia pulcherrima.*
Varietal denomination: 'Gala White'.

BACKGROUND OF THE INVENTION

The present invention comprises a new and distinct cultivar of *Euphorbia pulcherrima* known by the varietal name 'Gala White'.

The new cultivar was discovered in Florida as a naturally-occurring branch mutation of Poinsettia variety 'Gala Red' (U.S. Plant Pat. No. 14,994). The new variety was first asexually reproduced by tip cuttings in Florida and has been repeatedly asexually reproduced by tip cuttings thereafter. Continued observations from the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Compact and upright growth habit.
2. Little or no growth regulators needed.
3. Striking white variety with dark leaves and broad bracts.
4. Does not heat delay under high night temperatures during bud set.
5. Highly branched after the removal of the apical meristem which provides a display of bracts over the top of the plant.
6. Long lasting, retaining leaves and bracts for an extended duration when displayed indoors.
7. Desirable cyathia size and retention under stressful environmental conditions.

8. Strong branches that can hold large bracts and exhibit good branch angles.
9. Free from major diseases or insect problems.

The following characteristics distinguish the new Poinsettia from other cultivated Poinsettias of this type known to the inventor. The characteristics are described with comparative reference to parent cultivar 'Gala Red' (U.S. Plant Pat. No. 14,994).

1. 'Gala White' has 158D colored bracts, while 'Gala Red' has 45A colored bracts.
2. 'Gala White' has a leaf petiole color of 146D, while 'Gala Red' has a petiole leaf color of 184A.
3. 'Gala White' has a bract petiole color of 160C, while 'Gala Red' has a bract petiole color of 46A.
4. 'Gala White' has an anther color of 11B, while 'Gala Red' has an anther color of 185A.
5. 'Gala White' has a keeping quality of eight weeks or longer, while 'Gala Red' has a keeping quality of six weeks or longer.

The following characteristics also distinguish the new Poinsettia from other cultivated Poinsettias of this type known to the inventor. The characteristics are described with comparative reference to 'Festival White' (U.S. Plant Pat. No. 13,804).

1. 'Gala White' has 158D colored bracts, while 'Festival White' has 158C colored bracts.
2. 'Gala White' has a plant height of 24 to 26 cm, while 'Festival White' has a plant height of 25 to 30 cm.
3. 'Gala White' has a keeping quality of eight weeks or longer, while 'Festival White' has a keeping quality of six weeks or longer.
4. 'Gala White' has a leaf length of 12 to 13 cm and a leaf width of 8 to 9 cm, while 'Festival White' has a leaf length of 10 to 11 cm and a leaf width of 7 to 8 cm.

5. 'Gala White' has a bract length of 12 to 13 cm and a bract width of 9 to 10 cm, while 'Festival White' has a bract length of 14 to 15 cm and a bract width of 8 to 9 cm.

DESCRIPTION OF THE DRAWING

The accompanying photographic drawing illustrates the new cultivar, the color being as nearly true as possible with color illustrations of this type.

DESCRIPTION OF THE NEW PLANT

Figure 1:
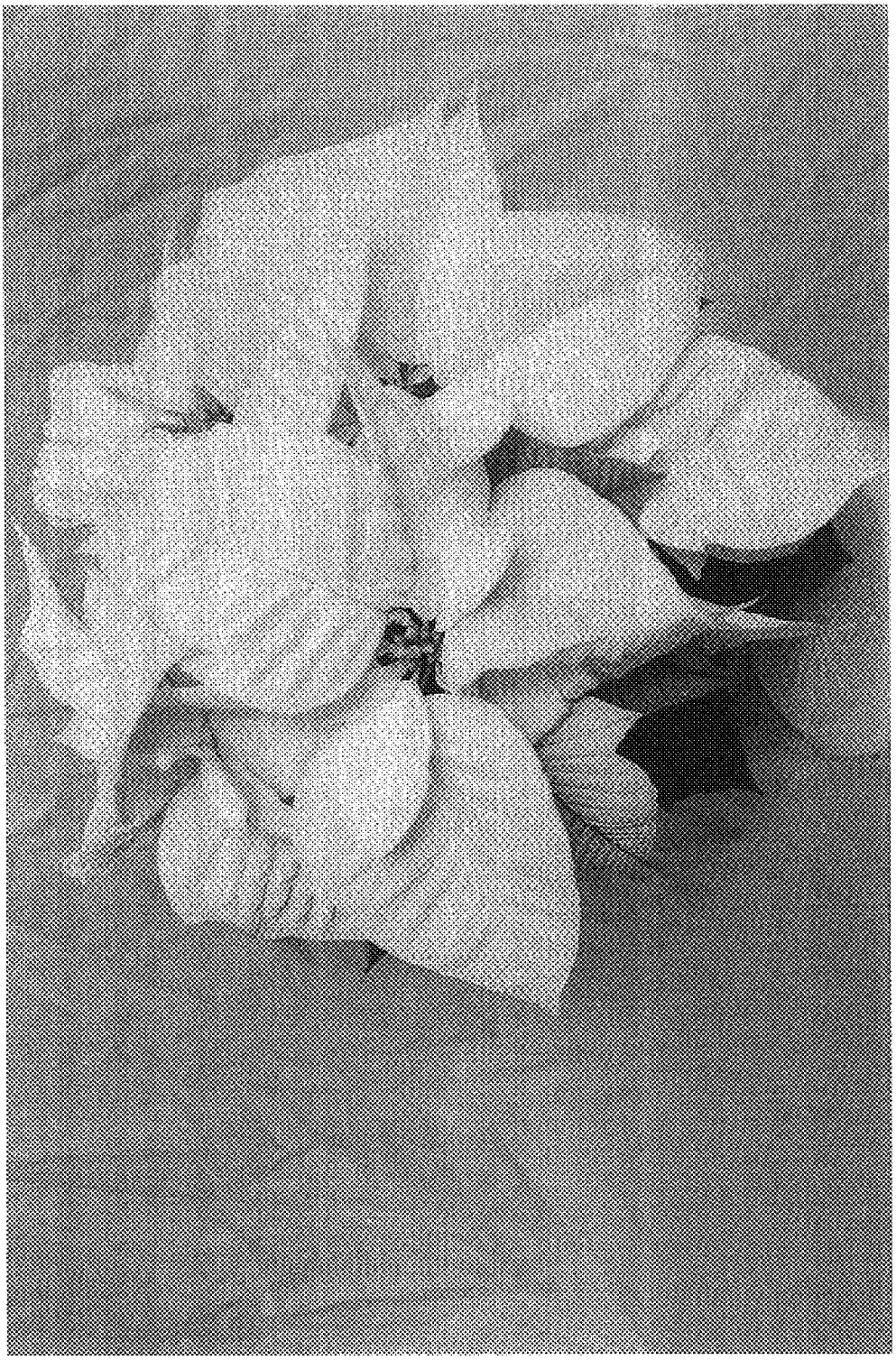

In the following description, color references are made to The Royal Horticultural Society Colour Chart, except where general terms of ordinary dictionary significance are used. Plants were grown during the winter of 2003 in Lompoc, Calif., in a double poly greenhouse. During the production of the plants, day temperatures ranged from 18 to 21° C., night temperatures ranged from 16.5 to 18° C. and light levels averaged from 3000 to 4000 foot candles of light. Rooted cuttings were planted in 15 cm containers and the new variety was approximately 13-14 weeks old when described.

Propagation:

*Type cutting.*—Tip cuttings.

*Time to initiate roots.*—Summer: About 14 days at 21° C. Winter: About 18 days at 21° C.

*Time to produce a rooted cutting.*—Summer: About 21 days at 21° C. Winter: About 25 days at 21° C.

*Time to produce a finished plant from planting.*—Approximately 14 weeks.

*Root description.*—Thick and fibrous, freely branching, moderately dense and white in color.

The plant:

*Classification.*—Botanical — *Euphorbia pulcherrima.* Commercial — 'Gala White'.

*Form.*—Upright and V-shaped plant habit.

*Plant height at flowering.*—About 24 to 26 cm.

*Plant diameter at flowering.*—About 45 to 50 cm.

*Growth rate.*—Moderate.

*Vigor.*—Good.

Branches:

*Branching habit.*—Branches from all nodes after pinching. The bottom breaks elongate faster than the top breaks. Pinching is required to enhance lateral branch development.

*Lateral branches.*—Number: Seven or more depending on the number of nodes left after pinching. Length: 18 cm. Diameter: 7 mm. Internode length: Generally from 1 to 2 cm, mostly 1 cm. Stem color: 146B. Texture: Glabrous.

Foliage:

*Leaf.*—Arrangement: Alternate. Number of leaves per lateral branch: Eleven. Shape: Ovate with deep lobing. Apex: Acuminate to acute. Base: Acute. Margin: Entire with lobing present. The lobing is oak leaf-like, with two lobes having a deeper cut at the basal end. Length: 12 to 13 cm. Width: 8 to 9 cm. Texture: Upper surface: Glabrous. Lower surface: Glabrous, but rugose because of protruding veins. Pubescence: Not present. Venation pattern: Pinnate. Young leaf color: Upper and lower surface: 146C. Mature leaf color: Upper surface: Deeper than 147A. Lower surface: 147B. Vein color: Upper surface: 147B. Midrib: 147B. Lower surface: 147C.

*Petiole.*—Length: 5.0 to 5.5 cm, but varies with the position on the stem. Diameter: 3 mm. Texture: Glabrous. Color: 146D.

Flower:

*Flowering habit.*—Over the top of the plant.

*Natural flowering season.*—November 25 to 30 in Lompoc, Calif. conditions.

*Time to flower.*—8 to 8½ weeks.

*Longevity.*—More than three months under greenhouse conditions and more than eight weeks under interior conditions.

*Inflorescence diameter.*—30 cm.

*Inflorescence height.*—3 to 4 cm.

*Fragrance.*—None present.

*Bracts.*—Number per inflorescence: 20 to 25 with continued development as the plant matures. Aspect: Flat to slightly drooping. Texture: Glabrous with slight rugose texture due to veining. Shape: Ovate. Apex: Acuminate. Base: Acute. Margin: Entire. Lobation: Not present. Length: 12 to 13 cm at maturity. Width: 9 to 10 cm. Young bract color: Upper and lower surfaces: 158C. Mature bract color: Upper and lower surfaces: 158D fading to 158C. Petiole: Length: 2.0 cm for lower bracts and 1.0 cm for upper bracts. Diameter: 3.0 mm. Color: 160C.

*Cyathia.*—Number per inflorescence: 10 to 15, but more develop as the plant ages. Diameter of cluster: 3 cm. Shape: Rounded. Length: 10 mm. Diameter: 5 mm. Color: Immature: 144B. Mature: 146B. Nectary: Number per cyathia: One. Size: 4 mm. Color: 17A. Peduncle: Length: 2 mm. Diameter: 1 mm. Angle: 45°. Strength: Strong. Texture: Glabrous. Color: 146C. Stamens: Quantity per flower: Over 50. Anther shape: Oblong. Anther size: 1 mm. Anther color: 11B. Pollen amount: Abundant. Pollen color: 21A. Pistils: Quantity per inflorescence: Five or more. Length: 8 mm. Style length: 2 mm. Style color: 144D. Stigma shape: Star-shaped with six points. Stigma color: 151A. Ovary color: 146C.

General:

Disease/pest resistance: No unusual disease or pest resistance observed.

Temperature tolerance: Plants of the new variety have been observed to tolerate low temperatures of 10° C. and high temperatures of 27° C.

Fruit or seed production: None observed.

I claim:

1. A new and distinct variety of Poinsettia plant named 'Gala White' as herein described and illustrated.

* * * * *